United States Patent [19]

Tucker et al.

[11] Patent Number: 4,712,540

[45] Date of Patent: Dec. 15, 1987

[54] CERVICAL COLLAR

[75] Inventors: Kevin M. Tucker; Donald Peeler, both of Toledo, Ohio

[73] Assignee: Jobst Institute, Toledo, Ohio

[21] Appl. No.: 21,629

[22] Filed: Mar. 2, 1987

Related U.S. Application Data

[63] Continuation of Ser. No. 734,981, May 16, 1985, abandoned.

[51] Int. Cl.⁴ .............................................. A61F 5/04
[52] U.S. Cl. ..................................... 128/76 R; 128/75
[58] Field of Search ............... 128/DIG. 23, 75, 76 R, 128/87 B

[56] References Cited

U.S. PATENT DOCUMENTS

| | | | |
|---|---|---|---|
| 3,313,297 | 4/1967 | Applegate et al. | 128/75 |
| 3,477,425 | 11/1969 | Grassl | 128/75 |
| 3,572,328 | 3/1971 | Bond | 128/75 |
| 4,413,619 | 11/1983 | Garth | 128/76 R |

FOREIGN PATENT DOCUMENTS 328537  1/1920  Fed. Rep. of Germany ... 128/DIG. 23

Primary Examiner—Charles Pearson
Assistant Examiner—Tonya Lamb
Attorney, Agent, or Firm—Stuart E. Krieger

[57] ABSTRACT

A cervical collar including a flexible panel and a member extending therefrom. The member is located against the outer surface of the panel when the panel is flat and flips over the panel to form a chin support member when the panel is formed into a neck encircling band.

22 Claims, 14 Drawing Figures

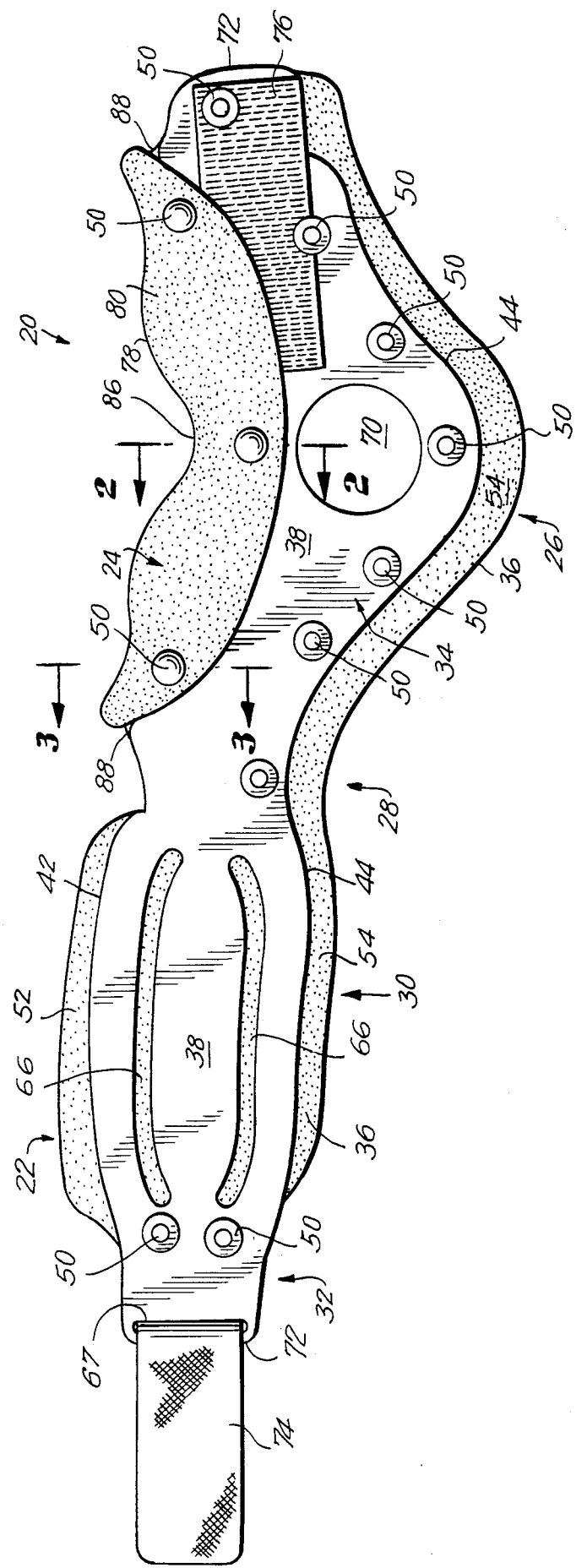

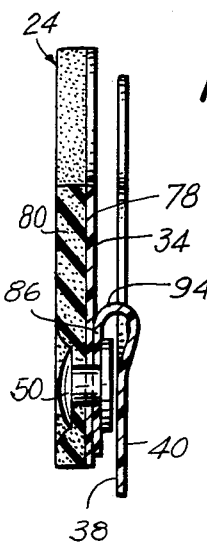
FIG.2
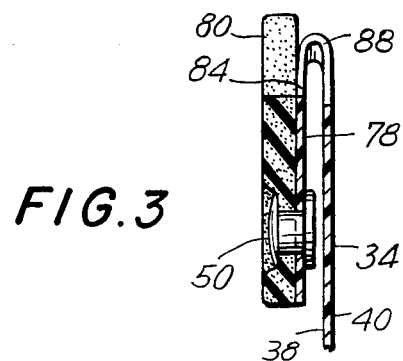
FIG.3
FIG.4
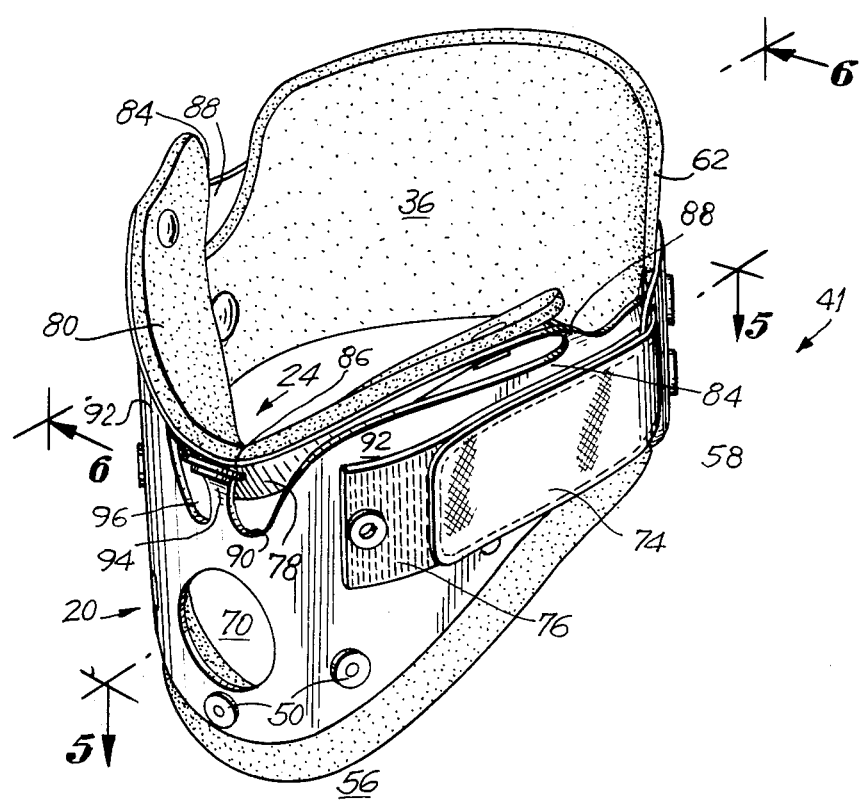

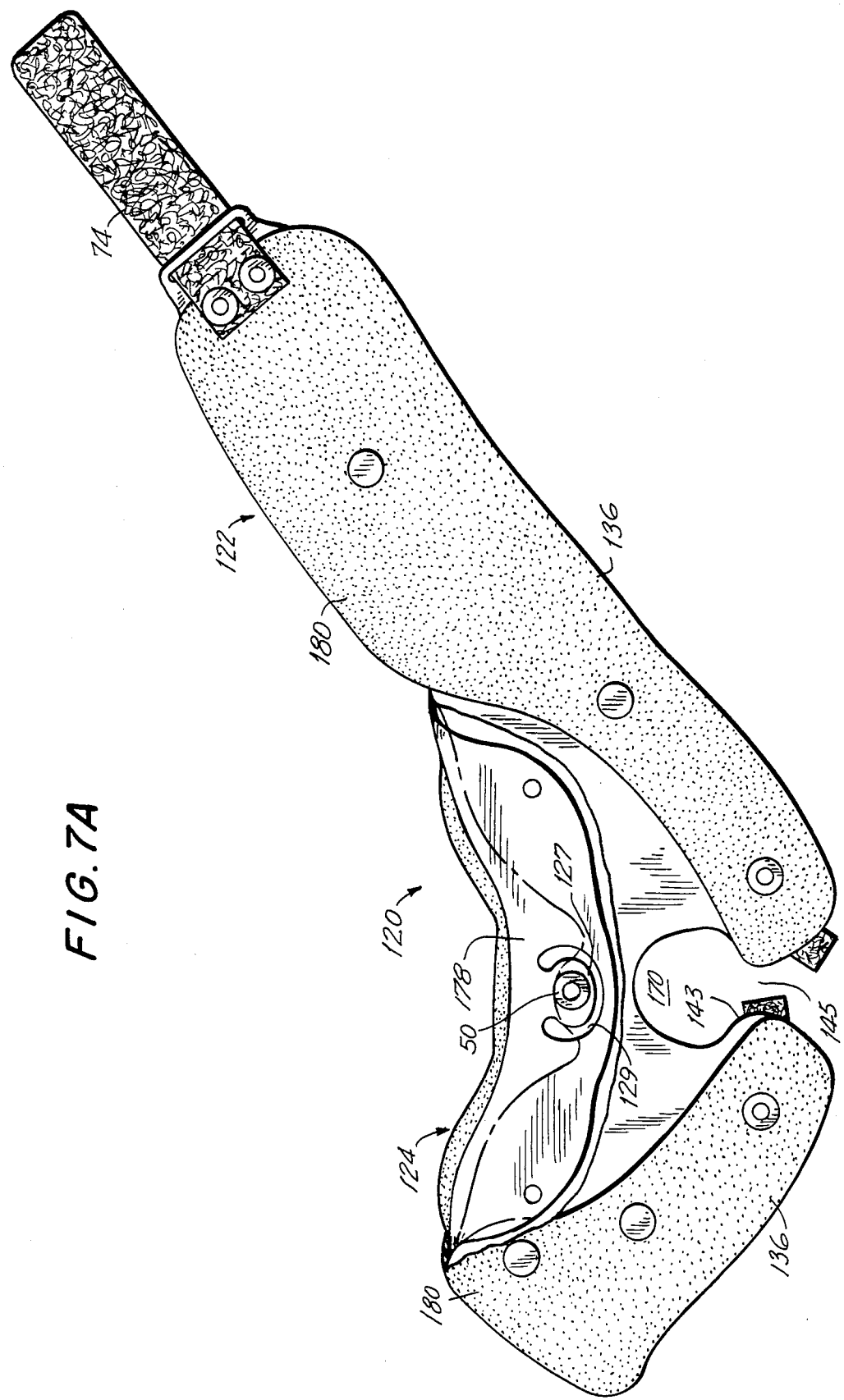

CERVICAL COLLAR

This is a continuing application of application Ser. No. 734,981, filed on May 16, 1985 now abandoned.

DESCRIPTION

FIELD OF THE INVENTION

This invention relates generally to cervical collars and more particularly to a cervical collar that can be stored in a flat configuration and that has a chin support that requires no assembly.

BACKGROUND OF THE INVENTION

The use of cervical collars in the treatment of various neck injuries is well-known in the art. Such collars basically function by holding the wearer's head in a particular position, while relieving the strain from the neck. In many emergency situations, such as automobile accidents, neck injuries can be diagnosed by paramedics. In such cases it is important to put a neck brace on the patient as soon as possible. Consequently the ease of storage of cervical collars on emergency vehicles and the ease of application to the injured individual are very important.

Traditionally, cervical collars have been thick and bulky in order to provide maximum support to the wearer's head. As a result, the storage of such devices on emergency vehicles has been limited. Attempts have been made to reduce the size of cervical collars to allow for storage of many such devices in a small area. U.S. Pat. No. 3,164,151 to E. D. Vera Nicoll describes a collar which is inflatable. When deflated the collar is relatively small and takes up little space in storage; however, this type of collar can be easily punctured, leaving it inoperative. Furthermore, if it is improperly inflated, it may not provide adequate support to the wearer's head. U.S. Pat. No. 4,413,619 to Geoffrey C. Garth describes another collar which requires little storage space; however, it includes a chin support that is secured to the neck encircling band and which requires assemblage to position the chin support in an operable position.

Accordingly, it is an object of the current invention to provide a cervical collar which requires little storage space, requires no assemblage of the chin support, and is effective in providing support to the wearer's head.

SUMMARY OF THE INVENTION

These and other objects are provided for by a cervical collar which includes a flexible panel that can be maintained in a flat configuration to facilitate storage and portability and can be easily formed into the operable configuration of a neck encircling band. A member is connected to the panel which is pivotable from a first position to a second position. In the first position, the member lies adjacent to the outer surface of the flat panel. Upon formation of the panel into a band, the member pivots over the top of the panel into the second position where it extends across the band to provide support to the wearer's chin. The panel can be retained in the band configuration by an appropriate fastening mechanism, such as by Velcro ® type strips located at each end of the panel which interlock upon suitable mutual contact of the strips.

BRIEF DESCRIPTION OF THE DRAWINGS

The foregoing and other objects, characteristics and advantages of the present invention will be more clearly understood from the following description when read in conjunction with the accompanying drawings in which:

FIG. 1 is a top plan view of a cervical collar taken in the open flat configuration in accordance with the present invention;

FIG. 2 is a view taken along line 2—2 of FIG. 1;

FIG. 3 is a view taken along line 3—3 of FIG. 1;

FIG. 4 is a view taken from the upper right of the cervical collar of FIG. 1 mounted in its operable configuration on a person, with the person shown in phantom;

FIG. 7A is a rear elevational view of the cervical collar shown in FIG. 7 with a portion broken away to show the chin support member;

DESCRIPTION OF THE PREFERRED EMBODIMENT

Figure 1A:
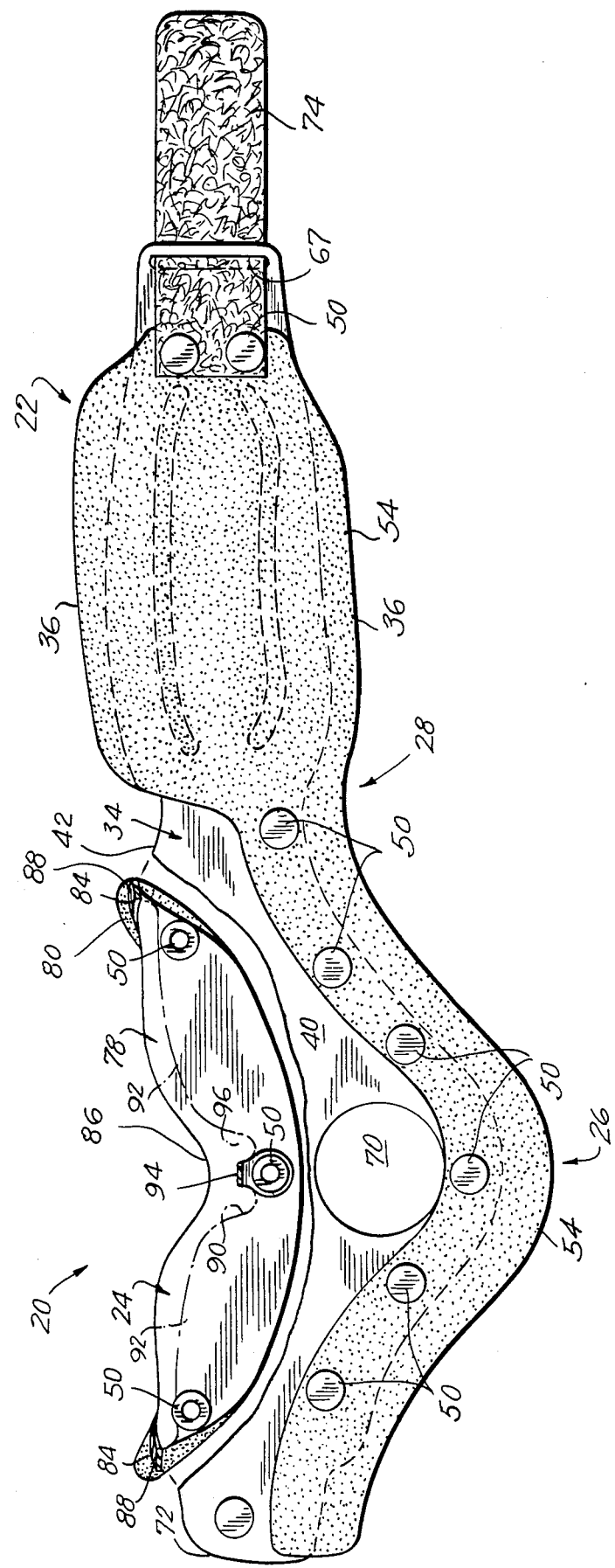
FIG. 1A is a rear elevational view of the cervical collar shown in FIG. 1 with a portion broken away to show the chin support member.

Referring now to the FIGS. 1-6 wherein a cervical collar in accordance with the present invention is generally indicated by the numeral 20 and includes a flexible panel 22 and a member 24 extending from the panel 22. The member 24, as described below, supports the wearer's chin when appropriately positioned. The panel 22 includes an anterior portion 26, an intermediate portion 28, posterior portion 30, and end portion 32. The panel 22 is preferably composed of a sheet 34 of plastic material, such as polyethylene, polyvinyl chloride or polypropylene, and a backing 36 of cushioning material, such as polyethylene or polyurethane foam.

The sheet 34 has an outer surface 38, inner surface 40 and top 42 and bottom surface 44. The backing 36 is secured against the inner surface 40 by a series of fasteners 50, such as rivets, extending through both the sheet 34 and backing 36. This arrangement causes the backing 36 to conform to the shape and configuration of the sheet, when it is in the flat configuration (FIGS. 1-3), or curled to form its operable configuration (FIGS. 3-6) of a neck encircling band 41.

Figure 5:
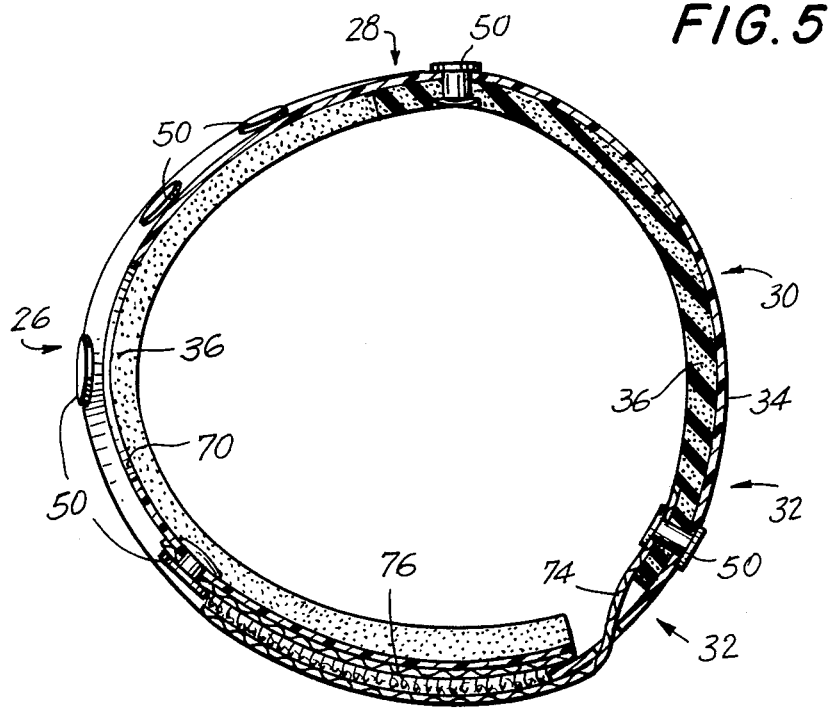
FIG. 5 is a view taken along line 5—5 of FIG. 4.
Figure 6:
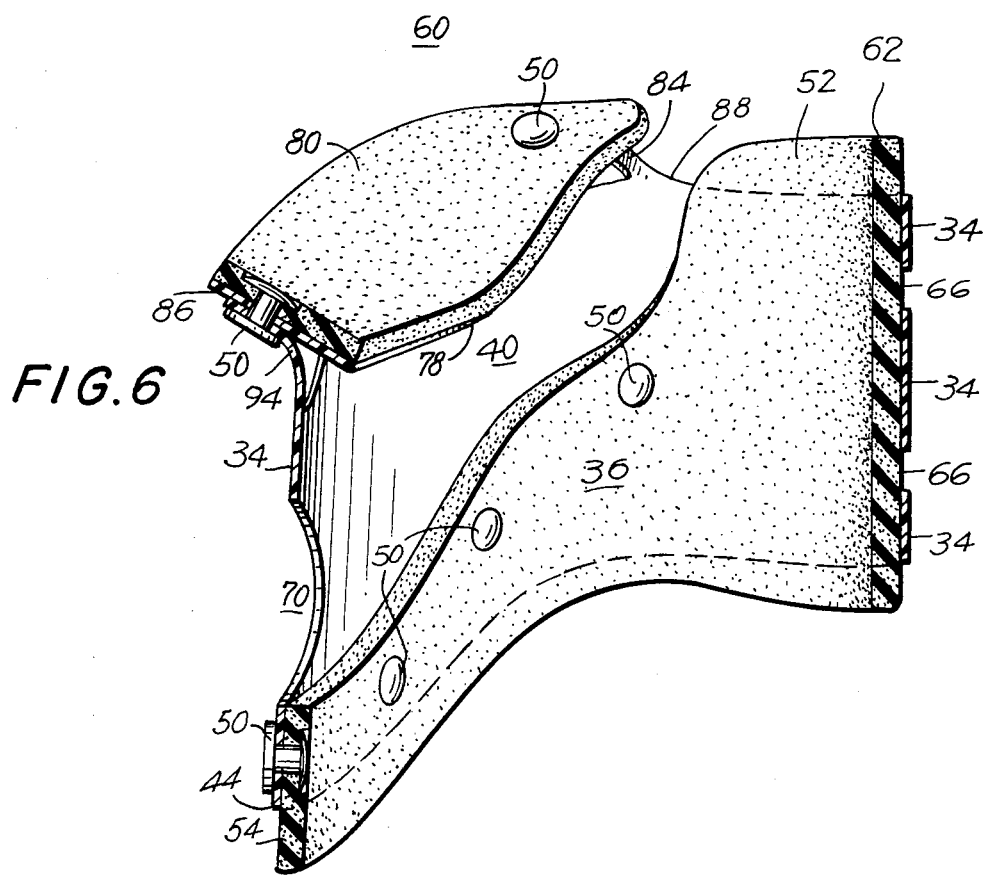
FIG. 6 is a view taken along 6—6 of FIG. 4.
Figure 7:
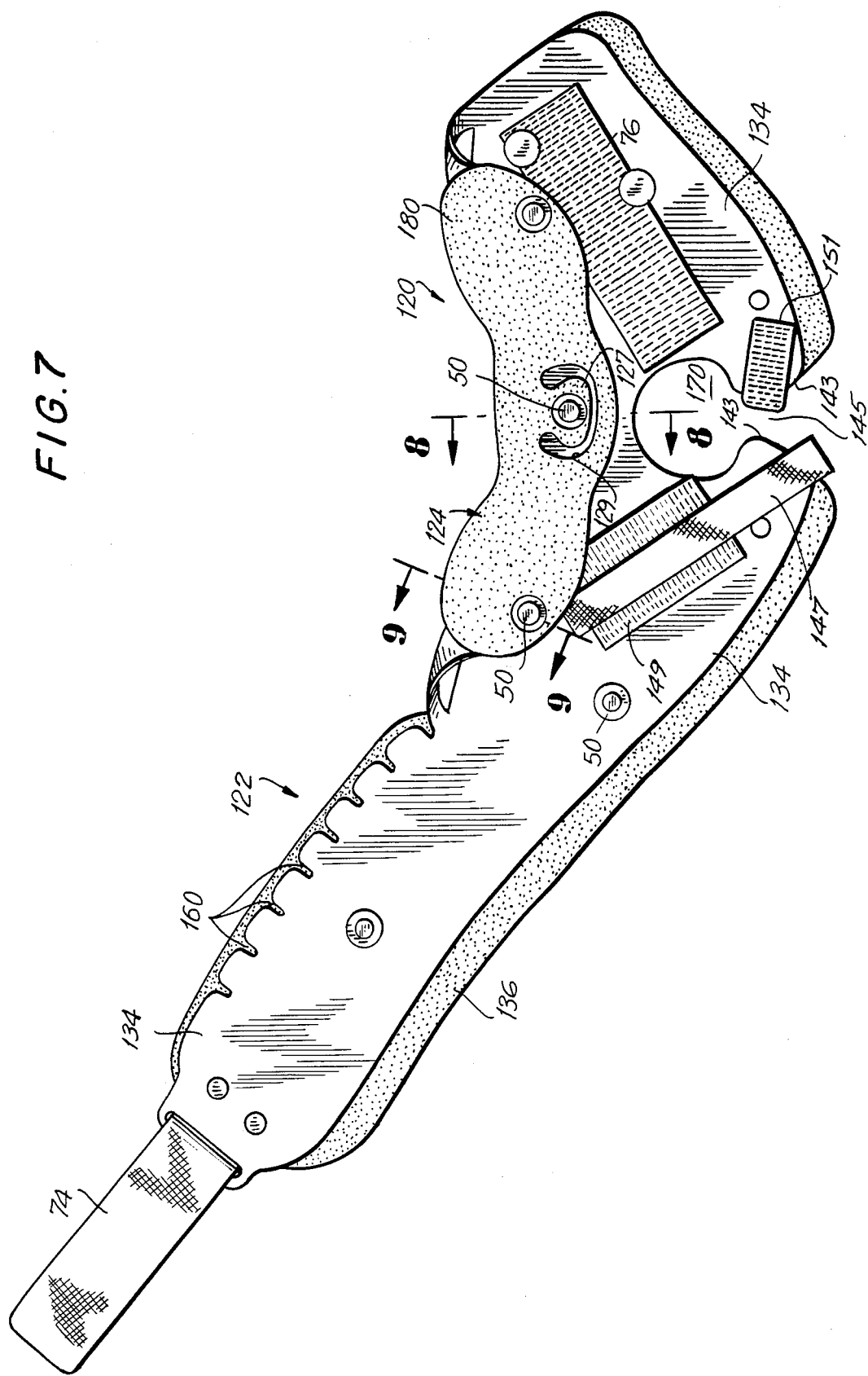
FIG. 7 is a top plan view of an alternative embodiment of a cervical collar taken in the open flat configuration, in accordance with the present invention.
Figure 8:
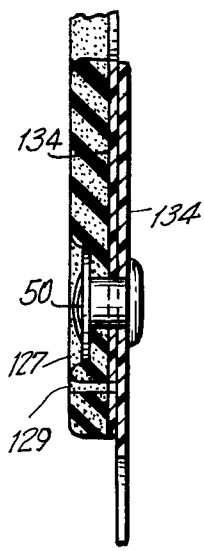
FIG. 8 is a view taken along line 8—8 of FIG. 7.
Figure 9:
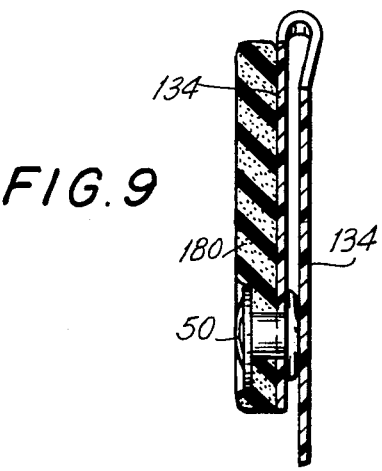
FIG. 9 is a view taken along line 9—9 of FIG. 7.
Figure 10:
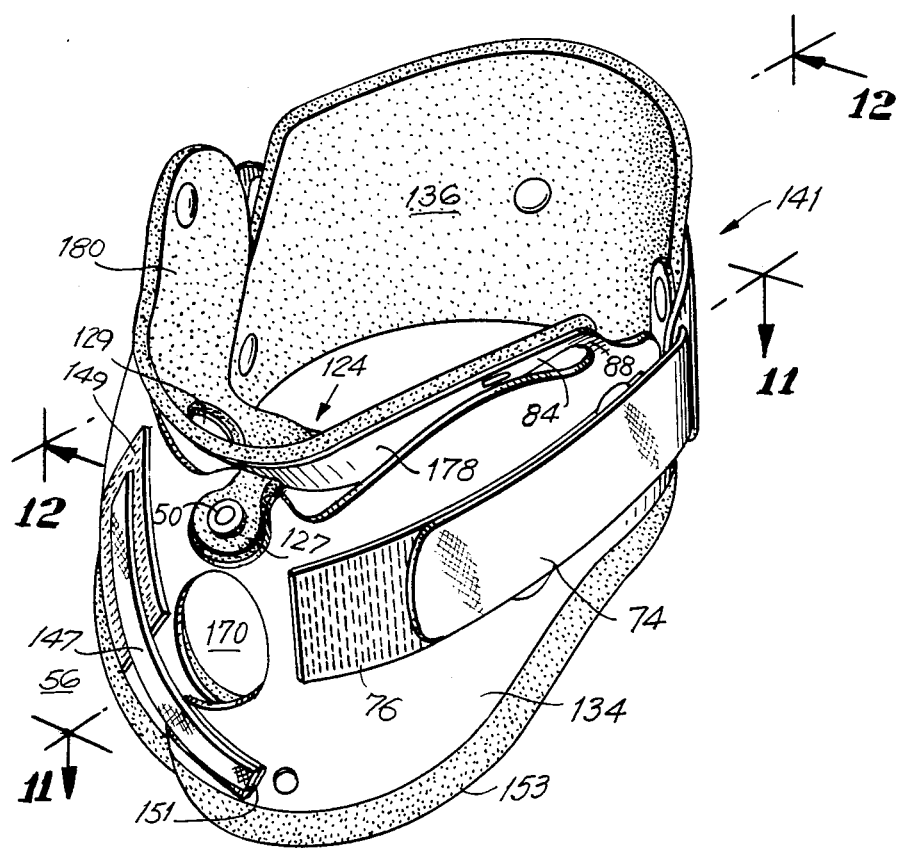
FIG. 10 is a view taken from the upper right of the cervical collar of FIG. 7 mounted in its operable configuration on a person, with the person shown in phantom.
Figure 11:
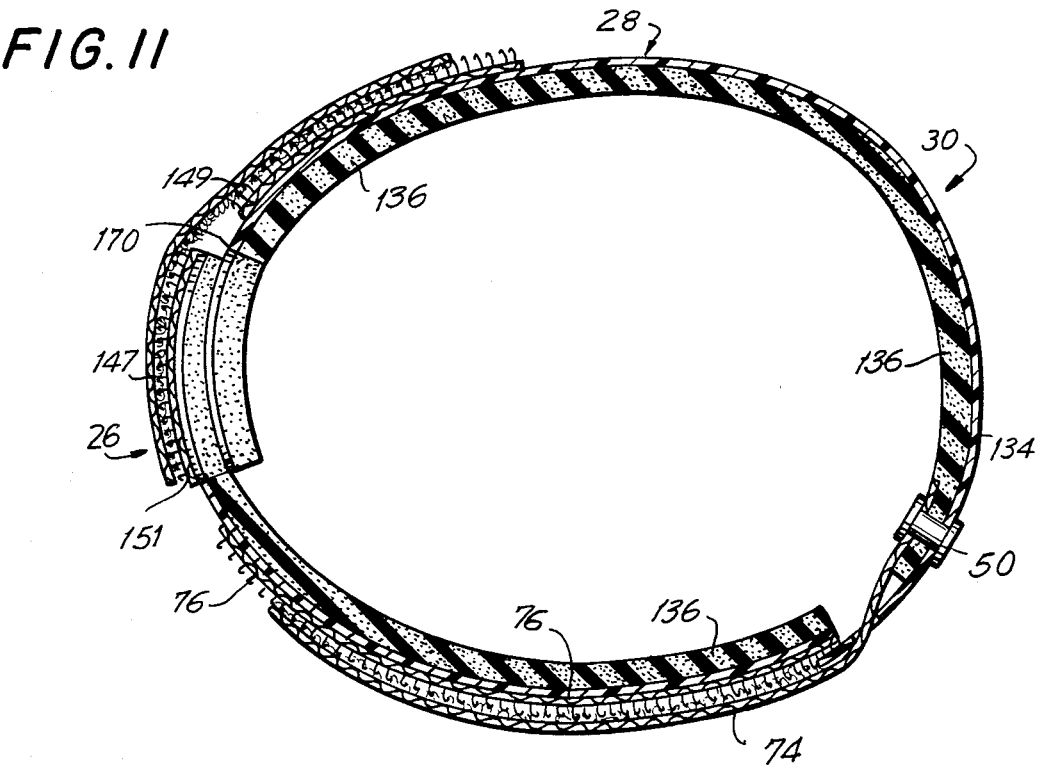
FIG. 11 is a view taken along line 11—11 of FIG. 10.
Figure 12:
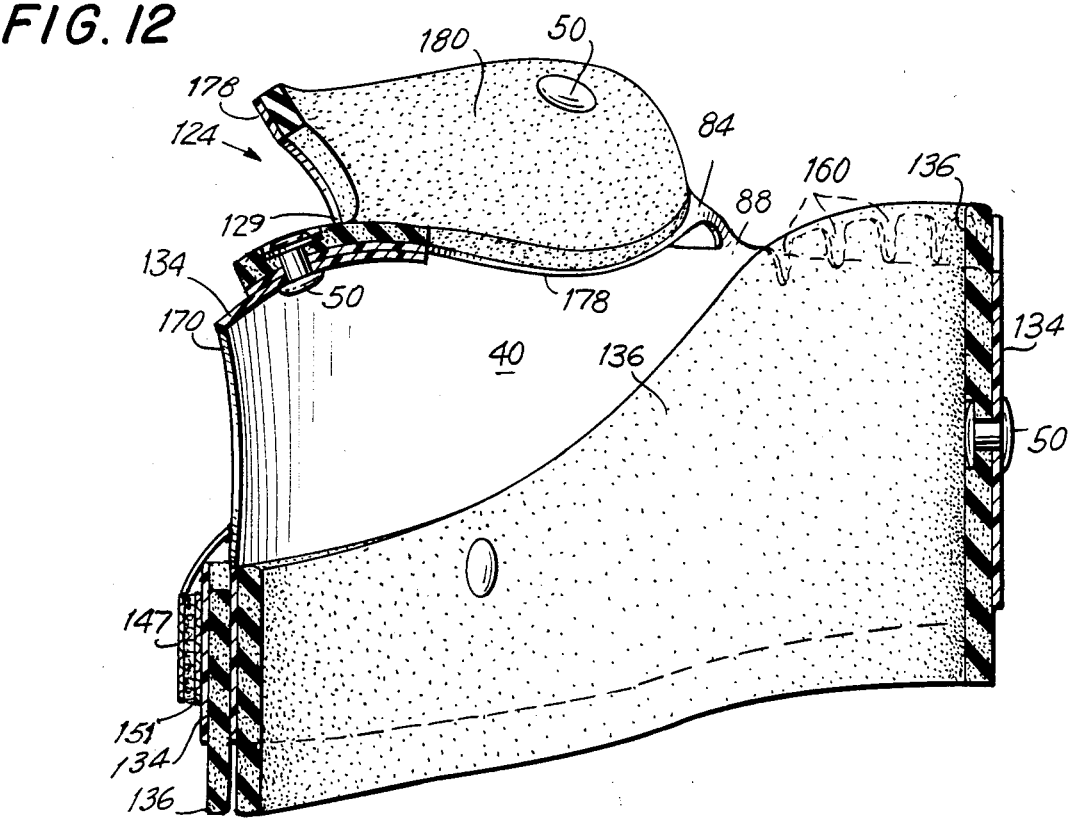
FIG. 12 is a view taken along line 12—12 of FIG. 11.

The backing 36 includes an upper region 52 which extends above the top edge 42 of the sheet 34 in the posterior portion 30 and a lower region 54 which extends beyond the bottom edge 44 of the sheet 34 along its entire length. In the operable configuration, as shown in FIGS. 4-6, the lower region 54 is in contact with the chest 56 and back 58 of the wearer 60 and the upper region 54 provides support for the back of the neck 62. The upper 52 and lower regions 54 of the backing 36 provide comfort which exceeds that obtained were the bottom 44 and top edges 42 of the sheet 34 in direct contact with the neck 62 and chest 56 of the wearer 60. It should be noted, however, that a panel 22 composed of a single sheet without backing would also function properly, however, typically less comfortably.

The sheet 34 includes two cut-out slits 66 which increases its flexibility thereby conforming to the contours of the occipital region and facilitates the formation of the panel 22 into the neck encircling band 41 shown in FIGS. 4–6. Extending through the panel 22 is an aperture 70 through which the trachea (not shown).

The panel 22 is equipped with a retaining means that retains the panel 22 in the configuration of the neck encirling band 41. The retaining means includes a fastener located near each opposing end 72 of the panel 22. A strip 74 of Velcro ® loop material is secured to the inner surface 40 of the panel 22 by fasteners 50, such as rivets. This strip 74 extends from the inner surface 40 of the panel 22 to the outer surface 38 through a slit 67 in the end portion 32 of the panel 22. Secured to the outer surface 38 of the anterior portion 26 of the panel 22 is a patch 76 of Velcro ® hook material. To form the panel 22 into the band 41 the strip 74 is interlocked with the patch 76. The utilization of the Velcro ® material permits size adjustment of the neck encircling band 41 which is dependent on the interlocked position of the strip 74 on the patch 76.

The member 24 is oblong in shape and includes a flexible strap 78 having a pad 80 of cushioning material secured thereto. The strap 78 has two end portions 84 and an intermediate portion 86. Each end portion 84 includes a ribbon 88 of flexible material which is connected to the sheet 34. The sheet 34 has a top surface portion 90 with a W-shaped curvilinear contour which includes two shoulders 92 and a central projecting tab 94. The tab 94 is connected to the intermediate portion 86 of the strap 78. A space 96 is defined between the strap 78 and top surface 42. The tab 94 and ribbons 88 are adequately flexible to permit the member 24 to be folded for positioning the member 24 adjacent the outer surface 38 of the sheet 34 as shown in FIG. 1.

The cervical collar 20 is typically stored and/or shipped in the flat configuration shown in FIG. 1 with the member 24 adjacent the outer surface 38 of the sheet 34. A portion of the strap 78 extends above the curvilinear contour of the top surface 42. When the cervical collar 20 is applied to the wearer or patient 60, the panel 22 is curled into a neck encircling band 41. When curled into the band 41, the member 24, using the top surface 42 as a fulcrum, pivots at least in part over the top surface 42 and moves into a position extending across part of the band 41 with the shoulders 92 providing underlying support for the strap 78. In this position, the member 24 gives support to the wearer's chin 98 (see FIG. 4).

The panel 22 encircles the wearer's neck 62 with the anterior portion 26 positioned by the front of the neck 62, the intermediate 28 and end portion 32 positioned at the side of the neck 62 and the posterior portion 30 positioned at the back of the neck 62. The retaining means secures the anterior portion 26 to the end portion 32 at the side of the neck 62 making it easier to install the cervical collar 20 on a patient 60 in a horizontal position.

Referring now to FIGS. 7–12 which show a second embodiment of a cervical collar that is generally designated by the numeral 120. As in the first embodiment, the collar 120 includes a panel 122 comprised of a sheet 134 having a backing 136 of cushioning material secured against the sheet 134, for example by fasteners 50 such as rivets. The panel 120 includes a plurality of grooves 160 cut into the sheet 134 which facilitates bending of the panel 120 from the flat configuration shown in FIGS. 7–9 into the operable configuration of the neck encircling band 141 of FIGS. 10–12. The panel 122 has an aperture 170 for tracheal access and a pair of opposing wings 143 located beneath the aperture 170 with a slit 145 extending therebetween. The slit 145 permits either spreading of the panel 120 so as to increase tracheal accessibility or overlapping of the wings 143 so as to decrease accessibility. Also, the spreading or overlapping affects the contour of the lower edge of the sheet 134 and backing 136 so that the wings' 143 orientation can be used for contour adjustment to insure that the panel 120 bears comfortably against the wearer's chest 56.

In order to maintain the wings 143 at the desired orientation the panel 120 is equipped with slit adjusting means. The slit adjusting means includes a fastener proximal to each of the opposing wings 143 and an interconnecting strap 147. A Velcro ® hook patch is mounted at 149 and 151 on the panel 120. A strap 147 of loop material is positioned on each of the patches 149, 151 while extending across the wings 143 and slit 145. The position of the strap 147 on the patches 149 and 151 determines and affects to a limited extent the contour of the chest contacting bottom surface 153 of the panel 122.

The cervical collar 120 is equipped with a member 124 which includes a strap 178 and padding 180. The member 124 is connected along end portions 84 by ribbons 88 of flexible material. The member 124 has a flexible drop leaf 127 or tab portion which extends downward from the member 124 and is attached by a fastener 50 to the central portion 186 of the sheet 134. The drop leaf 127 is cut from the member 124 leaving an aperture 129. The aperture 129 is adapted in configuration so as to comfortably accommodate and limit the undesirable movement of the patient's chin 98. The pivoting of the member 124 during curling of the panel 122 into a band 141, and retention of the panel 122, in the band configuration, functions similarly to the cervical collar 20 of FIGS. 1–6 described above.

We claim:

1. A cervical collar comprising:
   a flexible panel having an inner surface, an outer surface and a top surface interconnecting said inner and outer surfaces, said panel being formable from a flat configuration to a neck encircling band configuration;
   a chin support member connected to said panel and pivotable relative thereto from a first non-chin support position to a second chin support position, said member in said first position located adjacent to said outer surface of said panel, and responsive solely to formation of said panel into said neck encircling band configuration said chin support member pivoting over said top surface into said second position extending across said neck encircling band for providing support to a wearer's chin; and
   means for retaining said panel in said neck encircling band configuration.

2. The cervical collar of claim 1 wherein said panel has an aperture providing tracheal access.

3. The cervical collar of claim 2 wherein said panel has a slit communicating with said aperture, said slit being defined between two spaced apart opposing wing portions, said wing portions being spreadable to widen said slit or overlappable to close said slit.

4. The cervical collar of claim 3 wherein said panel includes means for adjusting and maintaining said wings in a predetermined position relative to each other.

5. The cervical collar of claim 4 wherein said means includes a patch of material at least proximate to each of said wings, a belt extending between said patches and positionable on said patches so as to interlock therewith and link said patches.

6. The cervical collar of claim 1 wherein said panel includes a flexible sheet having a front and rear surface and a backing made of a cushioning material affixed against said rear surface.

7. The cervical collar of claim 6, said panel having a width adequate to extend between the wearer's head and chest, said backing extending above said top surface to cushion said panel against the wearer's head.

8. The cervical collar of claim 7, said panel having a bottom surface, said backing extending below said bottom surface to cushion said panel against the wearer's chest.

9. The cervical collar of claim 6 wherein said retaining means includes two strips, one strip including a loop material, said other strip including hook material, each strip being positioned near an opposing end portion of said panel, said strips interlocking upon suitable mutual contact.

10. The cervical collar of claim 9 wherein one of said strips extends from an end portion, and said other strip is mounted on said front surface of said sheet.

11. The cervical collar of claim 6 wherein said chin support member includes a flexible strap, and a cushioning pad affixed to said strap.

12. The cervical collar of claim 11 wherein said strap has two opposing end portions and an intermediate portion therebetween, each of said end portions including a ribbon of flexible material connected to said sheet.

13. The cervical collar of claim 12 wherein said intermediate portion is connected to said sheet.

14. The cervical collar of claim 12 wherein said sheet and said strap are composed of the same material.

15. The cervical collar of claim 14 wherein said sheet and strap are an integral unit.

16. The cervical collar of claim 15 wherein said backing and pad are composed of the same material.

17. The cervical collar of claim 16 wherein said panel has a curvilinear top surface portion, said top surface portion and strap defining a space therebetween.

18. The cervical collar of claim 17 wherein said top surface has a tab projecting therefrom, said tab being connected to said intermediate portion of said chin support member.

19. The cervical collar of claim 18 wherein said tabs and ribbons are flexible, said chin support member being foldable so as to be positionable adjacent to said outer surface with said strap adjacent to said outer surface.

20. The cervical collar of claim 19 wherein said curvilinear top surface portion includes two spaced apart shoulder portions, said tab being located between said shoulder portions, said chin support member being supported by said shoulder portions when said panel is in said neck encircling band configuration.

21. The cervical collar of claim 20 wherein a portion of said strap extends above said tip curvilinear surface portion when said chin support member is folded, said panel being pivotable over said top surface, said top surface providing support to said chin support member when said panel is formed into said neck encircling band.

22. A cervical collar comprising:
a flexible panel having an inner surface, an outer surface and a top surface interconnecting said inner and outer surfaces, said panel being formable from a flat configuration to a neck encircling band;
a chin support member connected to said panel; and
means responsive solely to formation of said panel from a flat configuration to said neck encircling band for positively pivoting said chin support member from a position substantially parallel to said flexible panel to a position substantially perpendicular to said flexible panel, said means including a flexible strap having two ends, said flexible strap being secured to said flexible panel at both ends and at a point substantially midway between said ends.

* * * * *